(12) United States Patent
Ledoux et al.

(10) Patent No.: US 6,348,136 B1
(45) Date of Patent: Feb. 19, 2002

(54) METHOD AND APPARATUS FOR THE PURIFICATION OF VINYL AROMATIC COMPOUNDS

(75) Inventors: Marcus E. Ledoux; Kelli E. Prince; Adrian M. Jacobsen, all of Baton Rouge; Larry P. Braud, Jr., Gonzales, all of LA (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/514,492

(22) Filed: Feb. 29, 2000

(51) Int. Cl.[7] .............................. B01D 3/32; B01D 3/34; C07C 7/05; C07C 7/20
(52) U.S. Cl. .......................... 203/9; 202/154; 202/173; 203/8; 203/90; 203/78; 203/80; 203/DIG. 9; 585/805; 585/806; 585/807; 585/5
(58) Field of Search .................. 203/2, 3, 8, 9, 203/78, 80, 90, DIG. 9; 585/800, 5, 805, 806, 807; 202/154, 173

(56) References Cited

U.S. PATENT DOCUMENTS

| | | | |
|---|---|---|---|
| 4,166,773 A | * 9/1979 | Higley et al. | 203/72 |
| 4,177,110 A | * 12/1979 | Watson | 203/9 |
| 4,191,614 A | * 3/1980 | Watson et al. | 202/173 |
| 4,365,081 A | * 12/1982 | Shimizu et al. | 203/8 |
| 4,468,343 A | 8/1984 | Butler et al. | 252/403 |
| 4,469,558 A | 9/1984 | Watson | 202/154 |
| 4,492,675 A | 1/1985 | Watson et al. | 422/187 |
| 4,558,169 A | 12/1985 | Watson et al. | 585/440 |
| 5,772,854 A | * 6/1998 | Nelson et al. | 203/DIG. 25 |
| 6,096,941 A | 8/1999 | Art | 585/804 |
| 5,954,924 A | 9/1999 | Art | 203/1 |

* cited by examiner

Primary Examiner—Virginia Manoharan
(74) Attorney, Agent, or Firm—Roberts, Abokhair & Mardula

(57) ABSTRACT

The present invention is directed to an apparatus and method for the distillation of a readily polymerizable vinyl aromatic compound employing a polymerization inhibitor. The vinyl aromatic compound is subjected to distillation in at least one fractionation column having at least one reboiler for maintaining the bottoms of said column at a proper temperature. The reboiler includes a heating section and a vapor phase section. The bottoms fraction from the fractionation column is cycled to the reboiler and subjected to heat to vaporize at least a portion of the bottoms fraction to form a vapor phase in the vapor section, A slip stream of the bottoms fraction is introduced to the vapor phase section of the reboiler. The slipstream contains polymerization inhibitor that had been added to the process at the fractionation column. The invention reduces fouling at the reboilers. The slipstream is optionally introduced to the reboiler using one or more spray nozzles. The polymerization inhibitor is added to the fractionation column in sufficient amounts to maintain a concentration of at least 400 parts per million by weight in the bottoms fraction.

21 Claims, 2 Drawing Sheets

METHOD AND APPARATUS FOR THE PURIFICATION OF VINYL AROMATIC COMPOUNDS

BACKGROUND OF THE INVENTION

The present invention relates to a process and apparatus for improving the purification of vinyl aromatic compounds. More particularly, the present invention relates to a process and apparatus for the reduction in the formation of undesirable products in improving the utilization of polymerization inhibitor in the purification of vinyl aromatic compounds such as styrene, substituted styrene, divinylbenzene and polyvinylbenzenes. The improved utilization inhibitors result in a reduction in the amount of polymerized materials when the vinyl aromatic compounds are subjected to elevated temperatures such as in the distillation thereof.

It is well known that vinyl aromatic compounds such as monomeric styrene, lower alkylated styrene, e.g., alpha-methyl styrene, and divinylbenzene polymerize readily, and furthermore, that the rate of polymerization increases with increasing temperature. Inasmuch as styrene and divinylbenzene produced by common industrial methods contain impurities, these compounds must be subjected to separation and purification processes in order to obtain product suitable for most types of further industrial use. Such separation and purification is generally accomplished by distillation.

In order to prevent polymerization at the conditions necessary for the distillation of vinyl aromatic compounds, various types of known polymerization inhibitors have been employed in connection with distillation processes. For example, U.S. Pat. No. 4,469,558 to Watson shows a process for the purification of vinyl aromatic compounds and the utilization of dinitro-p-cresol (DNPC) as the polymerization inhibitor. U.S. Pat. No. 4,468,343 to Butler et al shows a process for the purification of vinyl aromatic compounds and the utilization of DNPC in combination with other components as the polymerization inhibitor. The inhibitor formulation is added to the various purification columns. U.S. Pat. No. 4,492,675 to Watson et al shows another process for the purification of vinyl aromatic compounds. The disclosures of these patents are hereby incorporated by reference in their entirety for purposes of U.S. prosecution. Other examples of inhibitors useful for inhibiting the polymerization of vinyl aromatics under distillation conditions include 4-tert-butylcatechol (TBC) and hydroquinone. It is preferred, however, to purify vinyl aromatics by using vacuum distillation techniques, whereby some of these processes and previously utilized inhibitors are rendered unsuitable in view of the fact that they are effective only in the presence of oxygen. Various inhibitors are well known in the art and range from sulfur to the more exotic and environmentally driven components. In a vinyl aromatic purification or distillation process, the residual material represents a significant pollution or waste removal problem.

However, the utilization of inhibitors must be controlled to minimize costs and in order to render these components useful in later processing. Most of these components are later subjected to controlled polymerization processes. For example, styrene is later utilized to make various polymers, including polystyrene. If the monomer is loaded with inhibitors, the polymerization process is adversely affected. Additionally, these additives add significant cost to the production process for vinyl aromatic compounds. Thus, there is a need to maximize the effect of any inhibitor that is utilized. In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains a significant problem today that the amount of polymer formed in the distillation apparatus and in the high purity product recovered there from is substantially higher than desired, and occasionally, that complete polymerization occurs inside of the distillation apparatus.

The purification of vinyl aromatic compounds such as styrene is normally carried out in multiple zones or columns. This allows the user to stage the purification conditions in order to maximize the recovery of the desired product. As indicated in the above referenced patents, styrene purification at a styrene plant takes place in three or more columns operated in series. Each purification section or column is equipped with its own reboiler configuration. Each reboiler is normally a steam heat exchanger that provides the required heat for the purification process.

It is therefore desirable to provide new processes for the maximization of the effect of polymerization inhibitors in the purification of vinyl aromatic compounds.

SUMMARY OF THE INVENTION

It is therefore an object of the present invention to provide a method for maximizing the effect of polymerization inhibitors in the purification of readily polymerizable vinyl aromatic compounds.

A further object of the invention is to provide a new and improved process for the distillation of readily polymerizable vinyl aromatic compounds, which process results in higher recovery of a high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus and particularly in the reboiler sections.

It is also an object of the present invention to provide a new and improved process for the distillation of vinyl aromatic compounds, which permits the distillation apparatus to be operated at an increased rate of throughput without a reduction in efficiency.

It is still a further object of the present invention to provide a new and improved process for the distillation of vinyl aromatic compounds, which provides all of the foregoing enumerated advantages in a vacuum distillation process.

In accomplishing the foregoing and other objects, there has been provided in accordance with the present invention a process useful for the distillation of a readily polymerizable vinyl aromatic compound comprising adding a solution of inhibitor to the vapor phase section of the reboiler apparatus utilized as part of the distillation apparatus.

In one aspect of the process according to the invention, the inhibitor is introduced into the distillation system by adding it to the distillation columns. A side stream from the bottom of the distillation column is added to the vapor phase section of the reboiler used with the column. The stream is preferably introduced to the vapor phase section through at least one spray nozzle added at the top of the reboiler. The stream is taken from the bottom of the distillation column and preferably contains at least 50 ppm of inhibitor. The inhibitor level is controlled by the addition of inhibitor to the various points in the distillation apparatus other than the reboiler. The amount of inhibitor necessary to effectively inhibit polymerization of the vinyl aromatic compounds may vary over a wide range depending upon various factors of the distillation process, e.g., temperature, reflux ratio, pressure, residence time, etc. Typically, however, it has been found that an amount of the inhibitor between about 50 and about 3000 ppm is sufficient to inhibit polymerization of vinyl aromatic compounds under normal distillation conditions (105° C., and above).

According to a further embodiment of the instant invention, also provided is a distillation method and apparatus for use with the purification of vinyl aromatic compounds. This method comprises introducing a feed of impure vinyl aromatic compound into a distillation apparatus; introducing an effective polymerization inhibiting amount of specified inhibitor into the distillation apparatus, and then distilling the feed under distillation conditions of elevated temperature through cycling the vinyl aromatic hydrocarbon through at least one reboiler (heat exchanger); and adding a side stream of the purification column bottoms to the top of the reboiler in the vapor phase section. This process allows the recovery of an overhead product of high purity vinyl aromatic product and a residual bottoms fraction having a reduced content of polymeric material.

In the preferred embodiment, the vinyl aromatic compound preferably comprises styrene, and is distilled in a distillation train comprising a benzene-toluene column, an ethylbenzene column, and a styrene column, although it is to be emphasized that the distillation method of the present invention is equally advantageous for use with other vinyl aromatic compounds and with other distillation equipment such as would be well known to those skilled in the art.

Through the use of the process according to the present invention, the amount of polymerization occurring within the distillation apparatus, and particularly within the reboiler, is significantly reduced in comparison to conventionally employed methods. In addition, the amount of desired distillation product is increased in proportion to the decrease in the amount of polymer formation.

Other objects, features and advantages of the present invention will become apparent from the detailed description of the preferred embodiments of the instant invention, taken in conjunction with the figures.

DESCRIPTION OF THE PREFERRED EMBODIMENTS

Figure 1:
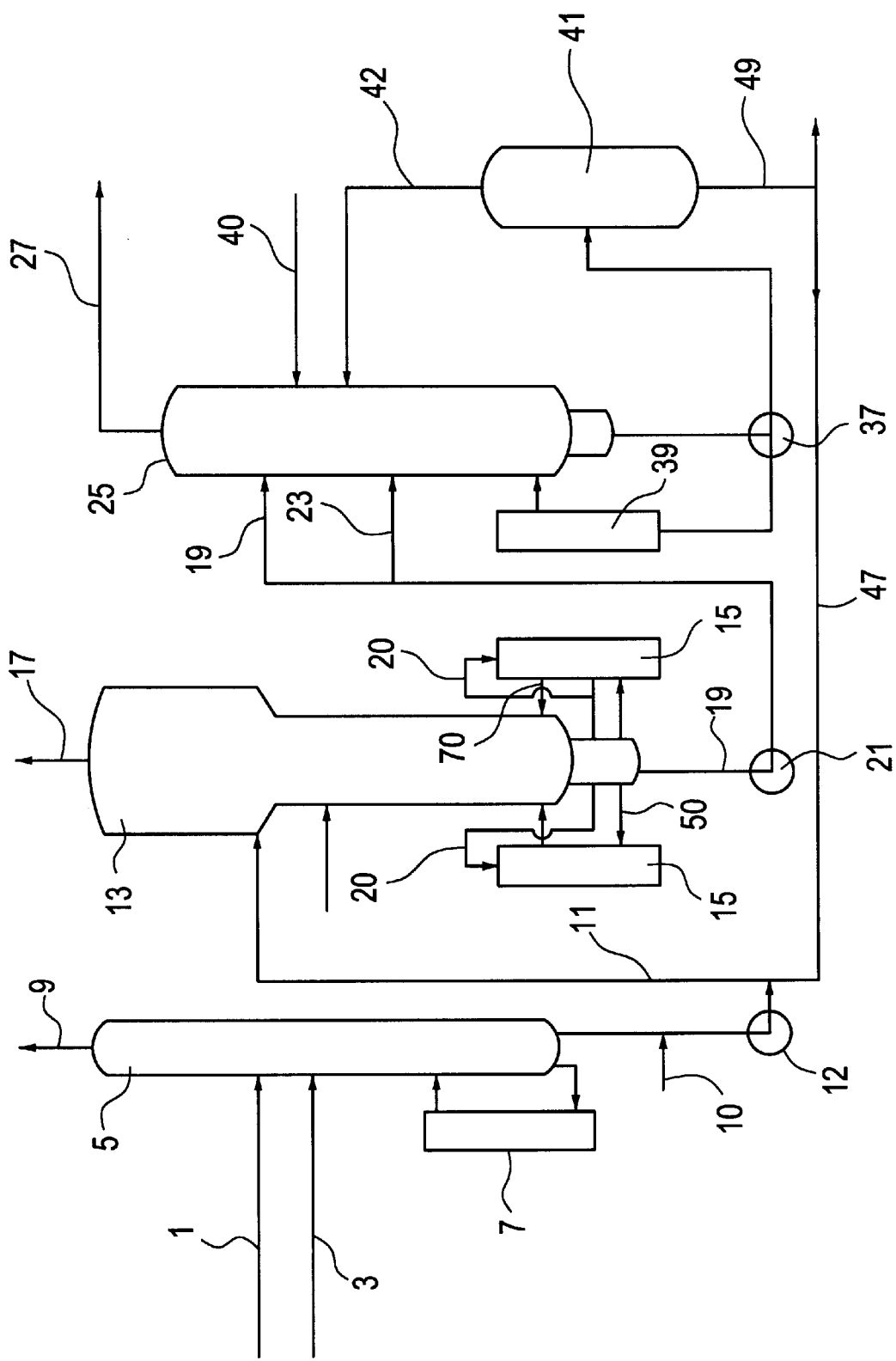
FIG. 1 is a schematic diagram of one embodiment of a distillation method of the present invention applied to a typical three column distillation train, comprising a first fractionation column, a recycle column, and a finishing column.

The distillation process of the present invention is employed for the purification or distillation of vinyl aromatic compounds. Typically, the distillation process is carried out under reduced pressure, e.g., vacuum distillation, and one of the significant advantages of the invention is reduction of byproducts that are formed in the distillation system without the use of additional polymerization inhibitors.

The distillation techniques of the process of the present invention are suitable for use in virtually any type of separation of a readily polymerizable vinyl aromatic compound from a mixture wherein the vinyl aromatic compound is subjected to temperatures above room temperature. The process of the present invention has been found particularly useful in vacuum distillation techniques, the preferred method for separating unstable organic liquid mixtures. In its most useful application, the distillation process of the present invention is applied to a distillation mixture containing one of the vinyl aromatic compounds selected from the group consisting of styrene, alpha-methylstyrene, vinyltoluene, vinylnaphthalene, divinylbenzenes and polyvinylbenzenes. The preferred application of the present invention relates to the distillation of crude styrene under vacuum distillation conditions.

The type and amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 ppm and about 3000 ppm by weight have generally provided suitable results, depending primarily upon the temperature of the distillation mixture and the degree of inhibition desired. More often, however, inhibitor concentration is from about 100 to about 1000 ppm.

The types of inhibitors useful for the present invention are well known in the art and include phenylene diamine, DNPC, asphaltenes, phenothiazines, phenolic compounds, nitrated phenols, and others. The particular inhibitor utilized is selected to from the group that is stable at the elevated temperatures in the reboiler as well as in the distillation column or columns. Mixtures of inhibitors are also utilized. Preferred inhibitors include dinitro butyl phenols such as 4,6-dinitro 2-sec-butyl phenol (DNBP), phenylene diamines such as n-(1,4-dimethylpentyl) N phenyl-p-phenylenediamine (PDA), or mixtures thereof.

During vacuum distillation of the styrene-containing mixtures, the temperature of any of the reboilers is preferably maintained from about 190° F. to about 290° F. by controlling reboiler pressure. The reboiler is usually a steam heat exchanger where steam is supplied through coils to heat any liquid in contact with the coils. Under such conditions, in a distillation apparatus having a distillation zone containing from about 50 to about 100 distillation stages, inhibitor mixture concentrations of from about 100 ppm to about 2000 ppm by weight are suitable, whereas concentrations of from about 200 ppm to about 1000 ppm by weight are preferable. In the case of styrene, 200 to 800 ppm by weight is preferable and concentrations in the range of from about 200 ppm to about 1000 ppm by weight are preferred for distillation of divinylbenzene. The foregoing ranges are based upon distillation temperatures of from 150° to 250° F. and residence times of between about 2 and 4 hours. In the lower portions of the temperature and residence time ranges, smaller amounts of inhibitor may be utilized. Amounts of inhibitor greater than those specified hereinabove may be employed, although the advantages of adding the additional inhibitor are not significant and are outweighed by the corresponding increase in cost.

The polymerization inhibitor of the present invention may be introduced into the distillation apparatus in any convenient manner that permits efficient distribution of the inhibitor throughout the apparatus. In operations for the purification of styrene, a distillation train comprising a benzene-toluene column, an ethylbenzene column, and a styrene or finishing column, is utilized. Additional columns are also utilized. For example, a distillation train includes multiple finishing columns and a recovery column. Each column utilizes at least one reboiler to provide the necessary heat. A reboiler comprises at least three sections. The bottom section is where the stream from the bottom of the associated distillation column is added. This stream comprises the material to be heated. The middle section comprises the coils where steam is utilized to heat the bottoms stream. Steam is introduced into the coils at about or above 280° F. in order to provide distillation column temperatures in the range of 200–250° F. The material flows upward from the coils section to the vapor phase section for return to the distillation column. This is the hottest section of the distillation operation. Prior art operations have led to the frequent fouling of this section.

For example, in styrene distillation, the ethylbenzene (EB) column reboilers are thermo siphon type reboilers and typically maintain a liquid level within the exchanger bundle and a heating media (steam or other) is used to vaporize styrene.

In a typical EB column, the liquid level in the bottom of the column and in the reboiler contains an inhibitor solution that prevents the formation of styrene polymer. As this liquid is heated in the reboiler and brought into the vapor state, the inhibitor typically remains in the liquid solution. As the vapor moves into the upper sections (vapor space) of the reboiler (and then into the distillation section of the column) small amounts of the styrene vapor solution will condense. The condensed material does not contain an inhibitor and is more prone to polymerize.

It was determined in accordance with one aspect of the invention that feeding a solution of inhibitor in the vapor space of the reboiler helps prevent polymerization of condensed styrene vapor when it comes in contact with the hot heat exchange surfaces.

The installation of spray nozzles (or other distribution device) that will spray a mist of inhibitor solution on the hot surfaces (shell and the tube bundle) protects the exchanger from fouling the heat exchange surfaces with polymer.

In a preferred embodiment of the present invention, a stream from the bottom of the EB column is introduced to the top of the reboiler. This is the same product that is introduced to the bottom of the reboiler for heating. This stream contains inhibitors that have been added to the system. As such, new inhibitor is not required. Any inhibitor present in this stream would reduce the amount of fouling discussed above. However, it is preferred that the amount of inhibitor added to the column is adjusted to provide a minimum inhibitor level of 200 ppm at the bottom of the column. Thus, the stream going to the top of the reboiler would have the same minimum 200 ppm of inhibitor. It should be noted that this is the same concentration in the stream going to the reboiler bottom section for heating and operations of the distillation system. Most preferred is a minimum inhibitor concentration of 400 ppm by weight.

The most economical method of the present invention is to control the inhibitor concentration at the bottom of the distillation column such as the EB column in styrene purification. Then the major bottoms stream is sent to the bottom of the reboiler for heating while a much smaller slip stream is sent to the top of the reboiler for preventing fouling. However, the present invention is still operable by adding a separate inhibitor stream to the vapor phase section at the top of the reboiler. This stream added to the reboiler section is not the controlling stream of inhibitor for the whole purification or distillation process. It is advantageous to add the bulk of the inhibitor to the top half of the distillation column.

Since the inhibitor stream is heavier that the stream to be purified, the inhibitor added at the top half of the distillation column would provide the greatest effect through its downward flow through the column.

Since the inhibitor is gradually depleted during distillation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. The means by which the maintenance of the necessary concentration of the inhibitor system is carried out is of no particular importance as long as the concentration of inhibitor is kept above the minimum required level.

Referring to the drawings, FIG. 1 illustrates the application of the distillation method of the present invention to a conventional styrene distillation train comprising a benzene-toluene fractionation column 5, referred to in the industry as a B-T column, an ethylbenzene or recycle column 13, and a styrene or finishing column 25, although it is to be emphasized that the operational principles of the instant distillation method are highly suitable for use, with minor modification, with the distillation equipment utilized in the purification of other vinyl aromatic compounds. As shown in FIG. 1, a heated crude styrene feed is introduced into the intermediate portion of B-T column 5 through feed line 1. The B-T column 5 may be of any suitable design known to those skilled in the art and may contain any suitable number of vapor-liquid contacting devices, such as bubble cap trays, perforated trays, valve trays, etc. Usually, however, B-T column 5 contains less than 40 distillation trays. Column 5 is also equipped with a suitable reboiler 7 for supplying heat thereto.

While most of the thermal polymer is formed in the ethylbenzene or recycle column 13, a small but significant amount of the total thermal polymer formed during distillation is formed in the B-T column 5. Accordingly, a polymerization inhibitor is essential within this column. To this end, the polymerization inhibitor may be introduced into the B-T column 5 as a separate stream through line 3, or it may be incorporated into the crude styrene feed flowing through line 1 for introduction into this column. When the polymerization inhibitor is added to the B-T column 5 as a separate stream, the inhibitor is preferably dissolved in a volatile aromatic hydrocarbon diluent. The volatile aromatic hydrocarbon diluent may comprise any suitable volatile aromatic hydrocarbon in which the inhibitor is soluble. By way of example, this diluent may include benzene, toluene, ethylbenzene, or styrene itself. Preferably, however, the volatile aromatic diluent comprises styrene, since use of this diluent permits the distribution of the inhibitor to correspond with the locus of distribution of styrene within the column. Generally, effective polymerization inhibition can be achieved by providing an inhibitor distribution that is coincident with the distribution of the readily polymerizable vinyl aromatic compound.

Under the distillation conditions imposed in column 5, an overhead stream comprising benzene and toluene is removed from the column via line 9. These low-boiling aromatic hydrocarbons are subsequently condensed and passed to storage for further use. The bottoms product in the B-T column, comprising styrene, ethylbenzene, inhibitor, and tar, serves as charge to the recycle or ethylbenzene column 13 and is introduced into the intermediate portion thereof by means of line 11 and pump 12. In order to reduce the viscosity of the B-T column bottoms product, a non-volatile hydrocarbon diluent may be introduced into line 11 and thence into recycle column 13 by way of line 10. Any suitable non-volatile hydrocarbon diluent may be used, the only requirements being that the non-volatile diluent is stable and sufficiently higher boiling than styrene for ready separation by fractionation. Typical materials used for this purpose include isopropylbenzene, butylbenzene, and xylene bottoms. Preferably, however, the non-volatile hydrocarbon diluent comprises a polyethylbenzene residue.

The ethylbenzene or recycle column 13 may be of any suitable design known to those skilled in the art and may contain from 40 to 100 trays. Preferably, however, the EB recycle column is of the parallel path design, i.e., two parallel distillation paths descending through the column. Additionally, it is also preferable that the recycle column contains a large number of trays in order to achieve a proper separation between the similar boiling styrene and ethylbenzene. The B-T bottoms are preferably introduced into the intermediate portion of the EB recycle column 13. The inhibitor that is present in the B-T bottoms that are charged thereto provides inhibitor protection within the ethylbenzene column 13. Additionally, the loading of inhibitor within this column is preferably supplemented by the recycle of tar thereto, as will be explained more fully hereinafter. Each side of the distillation column 13 also has connected therewith a reboiler 15.

In the most preferred embodiment, the EB column portion included three reboilers. As is shown in FIG. 1, each reboiler includes a feed line 50 that provides for the flow if fluid from the bottom of the EB column to the reboiler. A return conduit 70 reintroduces the treated fluid back to the EB column. Slipstream 20 is utilized to introduce the same stream to the vapor section at the top of the reboiler. In one embodiment of the present invention, each reboiler receives a slipstream at the rate of four gallons per minute (4 gpm) for a total of 12 gpm for all three reboilers. In another embodiment, the slipstream is introduced to each reboiler by employing four spray nozzles each having a capacity of one gallon per minute (1 gpm). Other distribution devices may be employed to maximize the amount of contact between the slipstream and the vapor phase. It is preferred to have an inhibitor concentration of from about 700–900 ppm in the slipstream.

The ethylbenzene overhead product of the recycle column 13 is withdrawn through line 17 and is subsequently condensed for reuse in an ethylbenzene dehydrogenation reactor. The recycle stream, comprising styrene, inhibitor, polyethylbenzene diluent if utilized, and tar is withdrawn from the bottom of the recycle column 13 through line 19. The recycle stream is then fed by pump 21 into the intermediate portion of the styrene or finishing column 25 through line 19. Optionally, the bottoms material may also be introduced into a lower portion of the styrene column 25 through line 23.

The finishing column 25 may be of any suitable design known to those skilled in the art. A typical column will contain, for example, about 24 distillation trays. A reboiler 39, preferably a forced flow reboiler, is also connected thereto in order to supply heat to the column. Due to the high viscosity of the styrene column bottoms, pump 37 is also preferably employed to circulate the bottoms through reboiler 39 and into styrene column 25. Generally, inhibitor protection is adequately provided in this column by the inhibitor present in the feed. Since, however, inhibitor is gradually removed from the distillation system, in order to insure adequate inhibitor protection throughout the distillation train, the inhibitor is preferably continuously added to the system through line 3, or in admixture with the crude styrene feed through line 1, and a portion of the tar is recycled at least back into the ethylbenzene column 13 in order to further supplement the amount of inhibitor within the system. Further addition of inhibitor to the styrene column 25, if desired, is achieved through line 40.

The high purity styrene overhead product withdrawn through line 27 from the styrene column 25 will generally be above 97% and even above 99% by weight styrene, depending upon the ultimate use. As has been mentioned, the high purity styrene overhead product is admixed with a polymerization inhibitor that is suitable to prevent polymerization during storage. The styrene column bottoms product is composed of polystyrene, undistilled styrene, polyethylbenzene, and the inhibitor. This fraction is withdrawn from the styrene column 25 into flash pot 41 for further processing. In the flash pot 41, residual styrene is removed from the bottoms from the styrene column and recycled back thereto as indicated by arrow 42. The tar produced in the flash pot 41 is withdrawn from the system on a continuous basis through line 49.

In one particularly preferred embodiment of the present invention, a portion of the tar, containing substantial amounts of the inhibitor, is recycled through line 47 for introduction into the ethylbenzene column 13. The portion of tar, which is recycled, may be added to the ethylbenzene column 13 by any method known to those skilled in the art. Best results are obtained, as has been discussed supra, by adding the tar at a location in the ethylbenzene column, which will give a distribution of inhibitor, which coincides with the distribution of styrene therein. Conveniently, this may be done by incorporating the recycled tar into the incoming feed for the ethylbenzene column 13, which flows through line 11. Optionally, additional inhibitor-containing tar may be recycled for introduction into the distillation train at other points, such as, for example, the B-T column 5. By recycling the inhibitor-containing tar, the inhibitor may thus be reused, accruing thereby a significant reduction in the process requirements for inhibitor. Moreover, tar recycle enables the inhibitor loading to be conveniently increased within the distillation train, particularly within the critical ethylbenzene column which has been shown to contribute approximately 80% of the total thermal polymer formed during distillation.

In this discussion of styrene purification, we have addressed the present invention as applied to the EB column. The vast majority of fouling or polymer formation is attributed to the EB column and the EB column reboilers. Thus, significant improvements are achieved by applying the present invention to the EB column reboilers only. Depending on the type of reboiler used for the other columns, the application of the invention to such reboilers may not yield significant return on the associated costs. Additionally, if fewer columns are employed for the purification of vinyl aromatic compounds, the present invention is applicable to one or two column systems.

Figure 2:
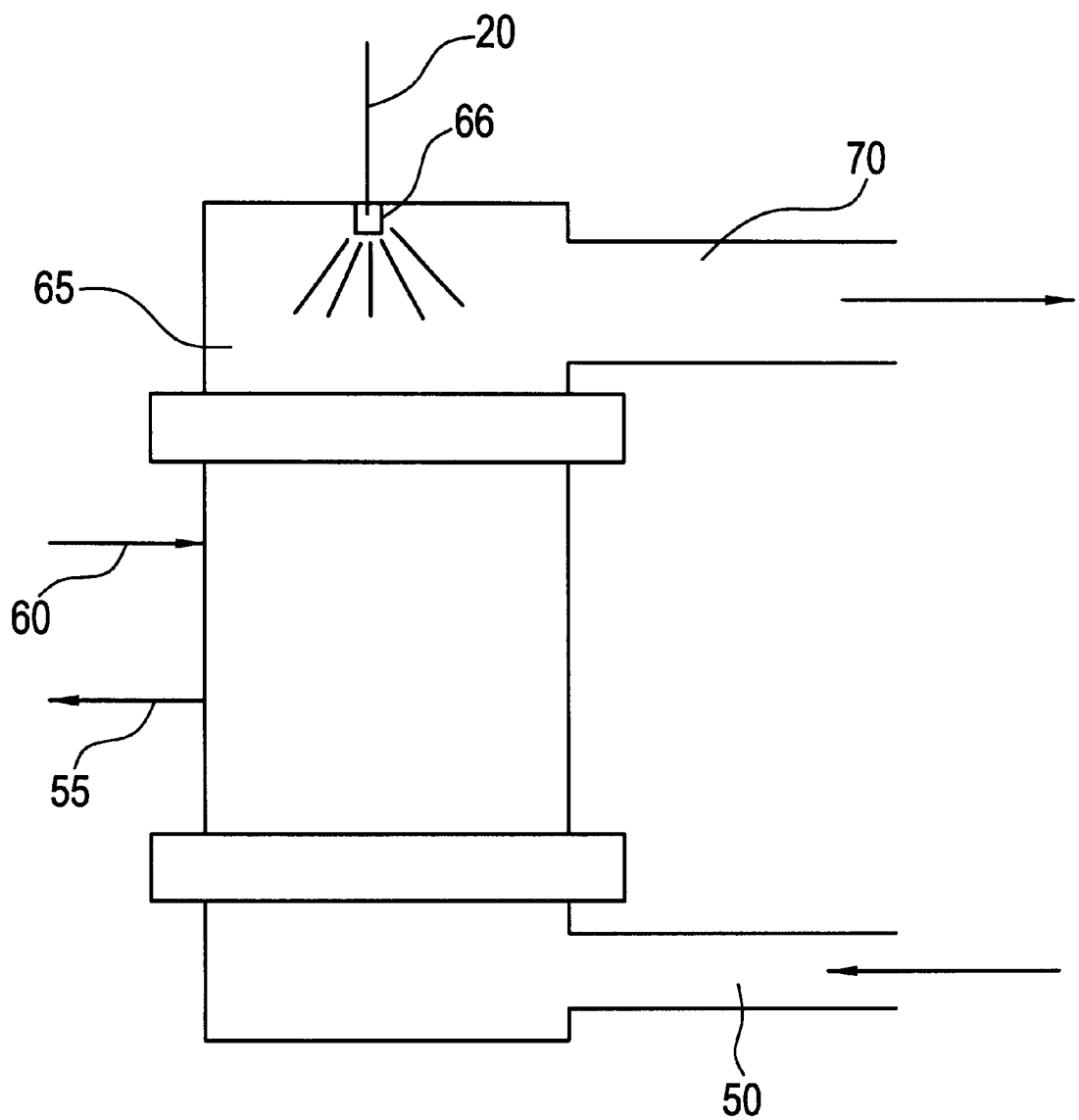
FIG. 2 is a schematic diagram of a reboiler employed in accordance with one embodiment of the present invention.

FIG. 2 illustrates one embodiment of the present invention as applied to the reboilers 15 shown in FIG. 1. In accordance with this embodiment, the reboiler is a thermo siphon type reboiler. This type of reboiler typically maintains a liquid level within the exchanger bundle and a heating media (steam or other) is used to vaporize the styrene. For example, in one embodiment of the present invention, the heat exchanger is a shell and tube heat exchanger with 500 to 1500 one-inch tubes inside a metal casing. The recycle stream is introduced to the reboiler through conduit 50. Steam is introduced through conduit 60 and the condensate is removed through conduit 55. The vapor section 65 is the most susceptible section for fouling. Conduit line 20 is shown for the introduction of the slipstream from the bottom of the purification column. The slipstream 20 is introduced to the vapor section 65 through a spray nozzle 66. Suitable nozzles include axial full cone medium capacity nozzles available from Lechler, Inc. Other nozzles may be utilized for the efficient distribution of the slipstream into the vapor section 65. In one embodiment 4 nozzles are utilized per reboiler. The heated stream is returned to the distillation column (EB column) through conduit 70. The slip stream is preferably introduced in quantities representing 2% or less of the main feed stream to each reboiler.

It should be noted that the present invention is applicable to other distillation configurations for the purification of vinyl aromatic compounds.

In one example of the present invention, a mixture of inhibitors comprising 60% DNBP and 40% PDA was utilized in a styrene purification train. The inhibitor mixture was introduced to the system as a solution of EB comprising 40% inhibitor and 60% EB. For this inhibitor system, it is preferred to maintain a concentration in the bottom of the EB column of not lower than 400–600 ppm of DNBP. Thus the minimum concentration of total inhibitor is higher due to the presence of PDA in addition to the DNBP. Preferably the DNBP concentration is maintained at not lower than 800 ppm. The slip stream going to the top of the reboilers represents about 0.2 to 2% of the regular stream fed to the bottom of the reboiler. For example, in a system using the DNBP/PDA inhibitors in an EB column using three reboilers, the feed to each reboiler is about one million pounds per hour. The slipstream fed to the top of each reboiler is about 1,350 pounds per hour. In this instance the composition of both of the feeds to the reboiler is over 98% styrene, less than 2% polymers and tar, and about 800 ppm inhibitor. This system significantly reduced the fouling in the reboilers.

Use of the distillation method of the present invention thus enables a distillation apparatus to operate with an increased rate as opposed to conventional prior art processes, since the fouling of the reboilers is significantly reduced. By minimizing the fouling of the reboiler sections, the amount of thermal polymer formed is substantially reduced over that occurring in conventional distillation processes. Consequently, higher distillation temperatures and higher pressures may be utilized without the formation of objectionable amounts of thermal polymer. In this manner, the rate of distillation may be increased without increasing the amount of polymerization that has been deemed to be acceptable in accordance with conventional distillation procedures. Additionally, downtime for the unit is reduced and longer operating cycles are achieved.

While the invention has been described in terms of various embodiments and specific examples, various modifications, substitutions and changes can be made without departing from the spirit of the invention. Accordingly, it is intended that the scope of the present invention be ascertained with reference to the following claims.

What is claimed is:

1. Apparatus for the distillation of a readily polymerizable vinyl aromatic compound employing a polymerization inhibitor comprising:

at least one fractionation column having reboiler means connected thereto for maintaining the bottoms of said column at a proper temperature, feed lines for introducing a vinyl aromatic compound into said column, and product lines for recovering an overhead product and a bottoms fraction therefrom;

the reboiler means comprising a heating section and a vapor phase section;

means for cycling the bottoms fraction to the reboiler means and subjecting the bottoms fraction to heat to vaporize at least a portion of said bottoms fraction to form a vapor phase in the vapor phase section; and means for introducing a slipstream of the bottoms fraction to the vapor phase section of the reboiler means.

2. The apparatus of claim 1 further comprising at least one spray nozzle for the introduction of the slipstream to the vapor phase section of the reboiler means.

3. The apparatus of claim 1 further comprising four spray nozzles for the introduction of the slipstream to the vapor phase section of the reboiler means.

4. Apparatus for the distillation of readily polymerizable vinyl aromatic compounds employing a polymerization inhibitor comprising:

a first fractionation column having reboiler means connected thereto for maintaining the bottoms of said column at a proper temperature, feed lines for introducing a vinyl aromatic compound into said column, and product lines for recovering an overhead product and a bottoms fraction therefrom;

a second fractionation column having reboiler means connected thereto, a feed line for transporting the bottoms of said first column to said second column for further distillation, and a product line for recovering an overhead product and a bottoms fraction;

a third fractionation column having reboiler means connected thereto, a feed line for transporting the bottoms of said second column to said third column for further distillation, and a product line for recovering an overhead product of high purity vinyl aromatic compound and a bottoms fraction;

wherein the reboiler means for said second fractionation column comprises a heating section and a vapor phase section;

means for cycling the bottoms fraction from the second fractionation column to the reboiler means and subjecting the bottoms fraction to heat to vaporize at least a portion of said bottoms fraction to form a vapor phase in the vapor phase section; and means for introducing a slipstream of the bottoms fraction to the vapor phase section of the reboiler means.

5. The apparatus of claim 4 further comprising at least one spray nozzle for the introduction of the slipstream to the vapor phase section of the reboiler.

6. A method for the distillation of a readily polymerizable vinyl aromatic compound employing a polymerization inhibitor comprising:

subjecting the vinyl aromatic compound to distillation in at least one fractionation column having at least one reboiler for maintaining the bottoms of said column at a proper temperature wherein the at least one reboiler comprises a heating section and a vapor phase section;

cycling the bottoms fraction from the at least one fractionation column to the at least one reboiler and subjecting the bottoms fraction to heat to vaporize at least a portion of said bottoms fraction to form a vapor phase in the vapor phase section; and introducing a slipstream of the bottoms fraction to the vapor phase section of the at least one reboiler.

7. The method of claim 6 wherein at least one spray nozzle is utilized for the introduction of the slipstream to the vapor phase section of the at least one reboiler.

8. The apparatus of claim 6 wherein four spray nozzles are utilized for the introduction of the slipstream to the vapor phase section of the at least one reboiler.

9. The method of claim 6 wherein the polymerization inhibitor is added to the at least one fractionation column in sufficient amounts to maintain a concentration of at least 400 parts per million by weight in the bottoms fraction.

10. A method for the distillation of readily polymerizable vinyl aromatic compounds employing a polymerization inhibitor comprising:

introducing the vinyl aromatic compound to a first fractionation column having reboiler means connected thereto for maintaining the bottoms of said column at a proper temperature, feed lines for introducing the vinyl aromatic compound into said column, and product lines for recovering an overhead product and a bottoms fraction therefrom;

introducing the bottoms fraction of the first fractionation column to a second fractionation column having at least one reboiler connected thereto, a feed line for transporting the bottoms of said first column to said second column for further distillation, and a product line for recovering an overhead product and a bottoms fraction;

introducing the bottoms fraction from the second fractionation column to a third fractionation column having reboiler means connected thereto, a feed line for transporting the bottoms of said second column to said third column for further distillation, and a product line for recovering an overhead product of purified vinyl aromatic compound and a bottoms fraction;

wherein the at least one reboiler for said second fractionation column comprises a heating section and a vapor phase section;

wherein the bottoms fraction from the second fractionation column is cycled to the reboiler and subjected to sufficient heat to vaporize at least a portion of said bottoms fraction to form a vapor phase in the vapor phase section; and introducing a slipstream of the bottoms fraction to the vapor phase section of the at least one reboiler.

11. The method of claim 10 wherein at least one spray nozzle is utilized for the introduction of the slipstream to the vapor phase section of the reboiler.

12. The method of claim 10 wherein four spray nozzles are utilized for the introduction of the slipstream to the vapor phase section of the reboiler.

13. The method of claim 10 the polymerization inhibitor is added to the fractionation column in sufficient amounts to maintain a concentration of at least 400 parts per million by weight in the bottoms fraction.

14. The method of claim 10 wherein the second fractionation column comprises a top half and a bottom half and wherein the polymerization inhibitor is added at least to the top half thereof.

15. The method of claim 10 wherein each fractionation column comprises a top half and a bottom half and wherein the polymerization inhibitor is added at least to the top half of each column.

16. The method of claim 10 wherein a polymerization inhibitor is introduced into the stream of vinyl aromatic compound entering the first fractionation column and wherein a second polymerization inhibitor is introduced to the slipstream.

17. The method of claim 10 wherein the slipstream is further introduced to the reboiler of the first and third fractionation columns.

18. The method of claim 10 wherein the vinyl aromatic compound is styrene.

19. The method of claim 18 wherein the second fractionation column is an ethylbenzene column and wherein said second fractionation column has three reboilers to heat the column.

20. The method of claim 19 wherein a slipstream is introduced to the vapor phase section of each of the three reboilers through at least one spray nozzle.

21. The method of claim 10 wherein the proper temperature of the bottoms of the fractionation column is from 190 degrees F. to 290 degrees F.

* * * * *